United States Patent [19]

Fouré

[11] 4,324,737

[45] Apr. 13, 1982

[54] PROCESS FOR THE PREPARATION OF ORGANOSTANNIC TRIHALIDES

[75] Inventor: Michel Fouré, Artix, France

[73] Assignee: Societe Nationale Elf Aquitaine, France

[21] Appl. No.: 151,642

[22] Filed: May 20, 1980

[30] Foreign Application Priority Data

May 23, 1979 [FR] France .................................. 79 13108

[51] Int. Cl.$^3$ ............................................... C07F 7/22
[52] U.S. Cl. .................................................. 260/429.7
[58] Field of Search ........................................ 260/429.7

[56] References Cited

U.S. PATENT DOCUMENTS 4,080,363  3/1978  Hutton et al. .................... 260/429.7
4,105,684  8/1978  Hutton et al. .................... 260/429.7

*Primary Examiner*—Helen M. S. Sneed
*Attorney, Agent, or Firm*—Ostrolenk, Faber, Gerb & Soffen

[57] ABSTRACT

A process of preparing organostannic trihalides by reaction of an olefin compound activated by a carbonyl group adjacent to the double bond, in the presence of a hydrohalic acid, with a stannous compound in a solvent-free medium and an excess of olefin which is at least 0.5 mol per mol of stannous compound.

Trihalides are obtained by this process; these trihalides may be converted into organostannic compounds for stabilizing compositions for halovinyl resins.

10 Claims, No Drawings

PROCESS FOR THE PREPARATION OF ORGANOSTANNIC TRIHALIDES

DESCRIPTION OF THE INVENTION

The present invention is an improvement in the production of certain organostannic trihalides from stannous compounds by the reaction of the latter with olefin compounds in the presence of hydrochloric acid. More particularly, it relates to the synthesis of organostannic trihalides in a solvent-free medium foreign to the reaction products. The organostannic trihalides are important raw materials in the manufacture of organic tin compounds used as stabilizers, particularly for polyvinylchloride.

In view of the well-known industrial utility of the organostannic trihalides, the methods of preparing these substances have been disclosed in numerous publications. Thus, French Pat. No. 2,285,392 describes a process which involves the reaction of a stannous halide and an olefin having a carbonyl group adjacent the carbon-carbon double bond, in the presence of a hydrogen halide. In carrying out this process, it was necessary to effect the reaction in a polar solvent, such as an alkyl ether and preferably diethyl ether. This process, therefore, involves the elimination of a solvent and the extraction of the pure product by means of another solvent.

Applicant has now found a way of avoiding these drawbacks, by proceeding in the absence of any solvent, and has found that the yields of organostannic trihalides obtained have been improved.

The process for the preparation of stannic trihalides is characterized by the fact that these compounds are obtained by reaction of a stannous compound with an excess of at least 0.5 mol of olefin with respect to the stannous compound, in the presence of a hydrohalic acid in a solvent-free medium.

The stannous compound may be a stannous halide (chloride, bromide, iodide) but also, and preferably, it is stannous oxide SnO, preferably in finely divided form.

The olefin compound is of the formula:

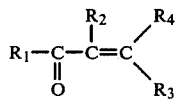

in which $R_2$, $R_3$, and $R_4$ represent hydrogen or an alkyl hydrocarbon radical containing from 1 to 3 carbon atoms, and $R_1$ represents an alkyl group, a hydroxyl or a hydrocarbon group containing oxygen. The organostannic trihalides obtained are of the formula:

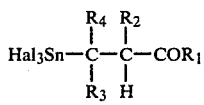

Among the olefins of the above formula are included, by way of illustration and not of limitation, methyl acrylate, ethyl acrylate, hexyl acrylate, acrylic acid, vinyl methyl ketone and methyl crotonate.

The halogen of the hydrohalic acid and of the stannous halide may be chlorine, bromine, iodine or fluorine but it preferably is chlorine; accordingly, hydrochloric acid and stannous chloride are preferably employed.

The amount of olefin used is in excess with respect to the stannous compound; it is between 1.5 mol and 6 mols to one mol of stannous compound. Excellent results are obtained when this amount is from 3.5 to 4.5 mols, and preferably when it is 4 mols of olefin to 1 mol of stannous compound.

It was not obvious that the reaction carried out in the absence of polar solvent and in the presence of an excess of olefin would lead to very good results. In fact, in French Pat. No. 2,368,498, which concerns the preparation of diorganostannic dihalides by the reaction of tin, hydrochloric acid and olefins activated by carbonyl groups, it is indicated that if the olefin is used at the same time as the solvent, extensive secondary polymerization reactions take place. The fact that proceeding in accordance with the invention in the absence of solvent and in the presence of an excess of olefin leads to the excellent results described in the Examples was therefore an entirely unexpected result.

The hydrogen halide is introduced in the form of a gaseous stream. The reaction temperature is between 15 and 70° C. and preferably about 25° to 30° C.; the process is carried out at atmospheric pressure.

The organostannic trihalide compounds prepared by the process of the present invention can be converted, as described in French Pat. No. 2,285,392, into organostannic compounds which stabilize polymeric vinyl halides by reaction of these trihalostannic compounds with organic fatty acids, maleic acid esters, alkyl thiols or mercapto esters, leading to compounds of the form $RSnA_3$ in which R represents the radical of the group consisting of the initial olefin and A represents the organic acid residue selected from the group consisting of alkyl $—S(CH_2)_nCOO$, in which n is 1 or 2, alkyl—S, alkyl—OCO and alkyl OCOH═CHCOO.

The organostannic compounds prepared by the method described in the present invention can also be converted into organostannic compounds which stabilize vinyl halide resins, as described in the patent of the Societe Nationale Elf Aquitaine filed of even date herewith, by reaction of the trihalostannic compounds with mercapto alkyl esters

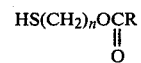

in which $R_6$ is an alkyl containing from 1 to 18 carbon atoms; it may belong to any aliphatic mono- or di-acid; however, the preferred esters are derived from fatty acids, particularly caprylic, pelargonic, capric, undecanoic, lauric, myristic, palmitic, stearic and isostearic acids, or mixtures of such acids.

The invention is illustrated by the following non-limitative examples:

EXAMPLE 1

33.8 g (0.25 mol) of stannous oxide and 86 g (1 mol) of methyl acrylate are introduced into a 500 ml threeneck flask provided with agitator, thermometer, condenser, gas-feed tube and an external cooling system. Vigorous agitation is effected, and the hydrochloric acid is introduced in gaseous form in such a manner that it is consumed as it is introduced. The temperature is maintained between 25° and 30° C. When the reaction mixture does not absorb any further HCl, the excess methyl acrylate is distilled. A residue remains which is purified by dissolving in chloroform, settling, drying over calcium chloride, and evaporation of the solvent. There are obtained 77.5 g, namely a yield of 99% referred to the tin oxide, of a white crystalline compound having the formula $Cl_3SnCH_2CH_2COOCH_3$. Its melting point is 71° C.

EXAMPLE 2

With the same apparatus and manner of operation as in Example 1, the methyl acrylate is replaced by 100.3 g (1 mol) of ethyl acrylate. There are obtained 82.4 g of a colorless oil identified by infrared analysis as being $Cl_3SnCH_2CH_2CO_2C_2H_5$. This compound is obtained in a yield of 100%.

EXAMPLE 3

With the same apparatus and method of operation as in Example 1, 67.5 g (0.5 mol) of stannous oxide and 250 g (2 mols) of methyl vinyl ketone are introduced into the flask; vigorous agitation is effected while introducing HCl in gaseous form. When the reaction is complete, the excess methyl vinyl ketone is distilled off. The product is purified in chloroform and there are obtained 144 g, namely a yield of 98%, of a white solid identified by spectroscopy as being $Cl_3SnCH_2CH_2COCH_3$.

EXAMPLE 4

The same procedure is employed as in the preceding examples; 67.5 g (0.5 mol) of stannous oxide and 144 g (2 mols) of acrylic acid are introduced into the flask. Gaseous HCl is introduced as rapidly as its absorption permits, while maintaining the temperature between 25° and 30° C. After the end of the absorption, the excess acrylic acid is distilled off under vacuum. The solid residue is purified in chloroform and after distillation of the latter there are obtained 146 g of a white solid the formula of which was identified by spectrography as being $Cl_3SnCH_2CH_2COOH$. Yield: 98% referred to the tin oxide.

EXAMPLE 5

The same procedure is used as in Example 1 but in the presence of solvent and without excess of methyl acrylate. 67.5 g (0.5 mol) of stannous oxide, 43 g (0.5 mol) of methyl acrylate and 200 ml of diethyl ether are introduced into the three-neck flask. Vigorous agitation is effected and the gaseous hydrogen chloride is introduced at the rate at which it is consumed, maintaining the temperature between 25° and 30° C. The ether is evaporated under vacuum. The product is dissolved in 250 ml of chloroform. After settling, the organic phase is dried over $CaCl_2$ and filtered, and the solvent and the volatile products are eliminated under vacuum. There are obtained 141 g (namely a yield of only 90% referred to the stannous oxide) of a white product which, redistilled, has a melting point of 73° C. It has the formula $Cl_3SnCH_2CH_2CO_2CH_3$.

EXAMPLES 6 TO 8

These tests were carried out by the use of the method described in Example 5, that is to say in accordance with the prior art, in the presence of a solvent and without excess of olefin, or with only a very slight excess. Example 6 was carried out with $SnCl_2$, the solvent being dimethoxy ethane; Example 7 was carried out with $SnCl_2$ in the presence of olefin and of diethyl ether as solvent; Example 8 was carried out with SnO, in the presence of dimethoxy ethane as solvent.

TABLE I

| Example No. | Olefin (1) | Stannous compound (2) | Molar ratio (1)/(2) | Solvent | Yield % |
|---|---|---|---|---|---|
| 1 | methyl acrylate | SnO | 4 | none | 99 |
| 2 | methyl acrylate | " | " | " | 100 |
| 3 | methyl-vinyl ketone | " | " | " | 98 |
| 4 | acrylic acid | " | " | " | 98 |
| 5 | methyl acrylate | " | 1 | diethyl ether | 90 |
| 6 | methyl acrylate | $SnCl_2$ | 1 | dimethoxy ethane | 89 |
| 7 | ethyl acrylate | $SnCl_2$ | 1.2 | diethyl ether | 79 |
| 8 | ethyl acrylate | SnO | 1 | dimethoxy ethane | 92 |

The results of Examples 1 to 8 are set forth in Table I. The comparison of the results shows that the best yields are obtained when the process is carried out by the method of operation described and claimed in the present invention.

What I claim is:

1. A process of preparing organostannic trihalides obtained by the action of a stannous compound on an olefin compound activated by a carbonyl group adjacent to the carbon-carbon double bond in the presence of a hydracid, characterized by the fact that the reaction medium is free of solvent but contains an excess of olefin, said excess being at least 0.5 mol per mol of stannous compound.

2. A process according to claim 1, characterized by the fact that the starting stannous compound is a stannous halide.

3. A process according to claim 1, characterized by the fact that the starting stannous compound is stannous oxide.

4. A process according to claim 1, characterized by the fact that the amount of olefin compound of the formula

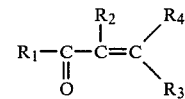

for the obtaining of

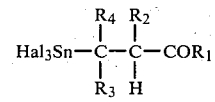

in which $R_2$, $R_3$, and $R_4$ represent hydrogen or an alkyl hydrocarbon radical containing from 1 to 3 carbon atoms and $R_1$ represents an alkyl group, a hydroxyl or a hydrocarbon group containing oxygen, is 1.5 to 6 mols per mol of stannous compound.

5. A process according to claim 4, characterized by the fact that the amount of olefin compound is 4 mols per 1 mol of stannous compound.

6. A process according to claim 4, characterized by the fact that the olefin is methyl acrylate, ethyl acrylate, hexyl acrylate, acrylic acid, vinyl methyl ketone or methyl crotonate.

7. A process according to claim 1, characterized by the fact that the hydracid is hydrochloric acid introduced in the form of a gaseous stream, the reaction temperature being between 15° and 70° C., and the process being carried out at atmospheric pressure.

8. A process according to claim 2, characterized by the fact that the starting stannous compound is stannous chloride.

9. A process according to claim 4, characterized by the fact that the amount of olefin compound is 3.4–4.5 mols per mol of stannous compound.

10. A process according to claim 7, characterized by the fact that the reaction temperature is between 25° C. and 30° C.

* * * * *